US006548726B1

(12) United States Patent
Sanderson et al.

(10) Patent No.: US 6,548,726 B1
(45) Date of Patent: Apr. 15, 2003

(54) REMOVAL OF DEHA FROM BUTADIENE STREAMS

(75) Inventors: John Ronald Sanderson, Austin, TX (US); Andrew Reusser, deceased, late of Beaumont, TX (US), by Mary Luz Reusser, legal representative; Steve Michalicek, Spring, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 09/669,982

(22) Filed: Sep. 26, 2000

(51) Int. Cl.$^7$ ............... C07C 7/12; C07C 7/00; B01D 61/00
(52) U.S. Cl. ............. 585/820; 585/809; 585/810; 210/660
(58) Field of Search ................ 585/820, 809, 585/810; 210/660

(56) References Cited

U.S. PATENT DOCUMENTS 6,093,285 A * 7/2000 Fernald et al. ............. 203/14
6,215,037 B1 * 4/2001 Padin et al. ............. 585/809

OTHER PUBLICATIONS

"Kirk–Othmer Ency. Chem. Tech.," 4:663–690, New York: John Wiley & Sons (Ed.) (1980).
"Ullmann's Encyclopedia of Industrial Chemistry," 5th Edition, A4:431–446, W. Gerhartz et al. (Ed.) year 1985.

* cited by examiner

Primary Examiner—J. Parsa
(74) Attorney, Agent, or Firm—Russ R. Stolle; Ron D. Brown; Nicole Peffer

(57) ABSTRACT

A method for removing diethylhydroxylamine (DEHA) from butadiene streams that does not leave an excessive amount of residual contaminates in the isolated butadiene stream. The DEHA is removed from the butadiene streams by ion exchange resins, which efficiently remove DEHA from the butadiene streams without causing the accumulation of an excessive amount of residual contaminants. To prevent polymerization of the butadiene upon removal of the DEHA, tert-butylcatechol (TBC) may be added to the butadiene stream before or after DEHA removal. Fresh or spent ion exchange resins may be used. After removal from the butadiene stream, the isolated DEHA can then be easily concentrated, and disposed or recycled. A method for removing DEHA from hydrocarbon streams is also disclosed.

30 Claims, No Drawings

REMOVAL OF DEHA FROM BUTADIENE STREAMS

TECHNICAL FIELD

This invention relates to the purification of butadiene streams, and, more particularly, to the removal of diethylhydroxylamine (DEHA) from butadiene streams.

BACKGROUND OF THE INVENTION

Butadiene is a $C_4$-unsaturated hydrocarbon that exists as two isomers. The 1,3-butadiene isomer is used in a variety of commercial applications, and is primarily used in the production of various polymers, such as styrene-butadiene rubber, polybutadiene, polychloroprene, nitrile rubber, acrylonitrile-butadiene-styrene, and styrene-butadiene latex. The 1,3-butadiene isomer is also used in the production of various chemicals, such as adiponitrile. By contrast, the thermodynamically less stable 1,2-butadiene isomer has virtually no commercial applications.

Butadiene may be manufactured using a variety of processes. In the past, butadiene was commonly prepared from acetylene or ethanol, or by the dehydrogenation of n-butane and oxydehydrogenation of n-butenes. Presently, butadiene is primarily produced as a by-product in the steam cracking of hydrocarbon streams to produce ethylene. Butadiene produced by steam cracking is typically then isolated from the other steam cracking by-products by fractional distillation and extractive distillation.

During butadiene isolation and separation, DEHA is commonly used as an inhibitor to prevent polymerization of the butadiene. Upon final isolation of the butadiene, DEHA is removed from the butadiene before it is used for commercial applications. Typically, DEHA is removed from the butadiene stream with a water wash, and then tert-butylcatechol (TBC) is added to the butadiene to prevent polymerization of the butadiene upon removal of the DEHA. However, using a water wash tends to cause the accumulation of an excessive amount of water in the isolated butadiene, which can interfere with subsequent applications of the butadiene. In addition, subsequent to its use, the water stream used in the water wash typically contains trace amounts of butadiene. Because the DEHA remaining in the water wash is difficult to isolate, the water stream must be properly disposed of, which can be costly because of the large volume of waste involved.

Therefore, what is needed is a method for removing DEHA from butadiene streams that does not leave an excessive amount of residual contaminates, such as water, in the isolated butadiene stream, and does not necessitate costly disposal fees.

SUMMARY OF THE INVENTION

Accordingly, the present invention is directed toward a method for removing DEHA from butadiene streams that does not leave an excessive amount of residual contaminates, such as water, in the isolated butadiene stream, and does not necessitate costly disposal fees. According to one embodiment of the present invention, DEHA is removed from butadiene streams by ion exchange resins. The use of ion exchange resins allows for the efficient removal of DEHA, without an accumulation of an excessive amount of residual contaminates. To prevent polymerization of the butadiene upon removal of the DEHA, TBC may be added to the butadiene stream before or after DEHA removal. After removal, the isolated DEHA can then be concentrated, and disposed or recycled.

In another embodiment, the present invention provides for the removal of DEHA from hydrocarbon streams by ion exchange resins.

DETAILED DESCRIPTION OF THE PREFERRED EMBODIMENT

In one embodiment, the present invention provides for a method of removing DEHA from butadiene streams. The method involves first providing a stream comprising primarily butadiene and a minor amount of DEHA. The stream is then contacted with an ion exchange resin to effectuate removal of the DEHA from the stream. After DEHA removal, a sufficient amount of TBC is added to the stream to prevent polymerization of the butadiene.

In another embodiment, the present invention provides for an alternate method of removing DEHA from butadiene streams. According to this method, a stream comprising primarily butadiene and a minor amount of DEHA is mixed with a sufficient amount of TBC to prevent polymerization of the butadiene upon removal of the DEHA. The stream is then contacted with an ion exchange resin to effectuate removal of the DEHA from the stream. Using this method, the ion exchange resin removes the DEHA, but does not remove a significant amount of TBC. As such, the butadiene stream remains inhibited during and after the DEHA removal process.

Typically, butadiene streams containing DEHA comprise primarily butadiene with a minor amount of DEHA. The term "minor amount" means that the butadiene/DEHA stream comprises less than about 100 ppm of DEHA. The term "primarily butadiene" means that the butadiene/DEHA stream comprises at least about 90% butadiene.

Preferably, the butadiene/DEHA stream is contacted with the ion exchange resin in a fixed bed reactor that has been charged with the ion exchange resin. However, the DEHA removal process may be conducted using a variety of other processing equipment to achieve substantially the same results.

Preferably, the ion exchange resin comprises a conventional acid resin. More preferably, the ion exchange resin comprises Amberlyst®-15, Amberlyst®-35, Amberlyst®-36, Amberlyst® XN-1010 (all from the Rohm and Haas Company), or Dowex®-50WX2 (from the Dow Chemical Company). Advantageously, the embodiments of the present invention are operable with fresh or spent resins. The term "spent resins" refers to resins that have been used in other applications, and are no longer suitable for such applications because of the resin's reduced activity. The spent resin may have been previously used in any number of applications, such as, but not limited to, the preparation of methyl-tert-butyl ether (MTBE), provided that such applications do not totally consume all of the active sites on the resin.

Preferably, the DEHA removal process should be conducted within a temperature range from about 0° C. to about 110° C. More preferably, the DEHA removal process should be conducted within a temperature range from about 15° C. to about 50° C.

Preferably, the DEHA removal process should be conducted at a pressure from about atmospheric pressure to about 2000 psig. More preferably, the DEHA removal process should be conducted at a pressure from about 50 psig to about 150 psig.

Preferably, if TBC is added to the butadiene stream before the DEHA is removed from the stream, a sufficient amount of TBC should be added so that before purification the stream contains at least about 5 ppm of TBC. If TBC is added to the butadiene stream after the DEHA is removed from the stream, a sufficient amount of TBC should be added to the effluent collection vessel so that the isolated butadiene stream contains at least about 5 ppm of TBC.

After removal from the butadiene stream, the isolated DEHA can then be concentrated, and disposed or recycled.

It is understood that several variations may be in the foregoing without departing from the scope of the invention. For instance, while the embodiments of the present invention are primarily discussed as being used to remove DEHA from butadiene streams, the present invention should not be construed as being limited to use with butadiene. The embodiments of the present invention may be used to remove DEHA from a variety of other hydrocarbons, or mixtures thereof. In most instances, the hydrocarbon will comprise an unsaturated hydrocarbon because DEHA is most often combined with such hydrocarbons to prevent their polymerization. In this embodiment, a stream comprising a hydrocarbon, or mixtures thereof, and a minor amount of DEHA, relative to the amount of the hydrocarbon in the stream, is contacted with an ion exchange resin to effectuate DEHA removal from the stream.

In addition, the embodiments of the present invention may be used in conjunction with other purification methods, including, but not limited to, the water wash method. If used in conjunction with another purification method, the embodiments of the present invention may be used prior to, or subsequent to, the other purification method(s). Other purification method(s) may be necessary to remove other residual impurities contained in the stream.

The following examples are illustrative of the present invention, and are not intended to limit the scope of the invention in any way.

EXAMPLE 1

A butadiene feed containing DEHA was run through a 50 mL stainless steel up-flow reactor. The reactor was operated at 85 psig and at ambient temperature. For each run, 50 mL of fresh resin were charged to the reactor. A small amount of TBC was added to the effluent tank to prevent polymerization of the butadiene upon DEHA removal. Periodically, a sample of the reactor effluent was collected and analyzed. Table 1 details the results.

TABLE 1

| Resin | Time (hr) | Temperature (° C.) | Feed Rate (g/hr) | DEHA in effluent (ppm) | Water in effluent (ppm) |
|---|---|---|---|---|---|
| Amberlyst ®-35 (fresh) | 0.0 | — | — | 3.56 | 320 |
| | 4.0 | 23.3 | 88 | 0.02 | 147 |
| | 5.5 | 23.3 | 124 | 0.00 | 149 |
| | 7.0 | 23.2 | 106 | 0.00 | 1019 |
| Amberlyst ®-35 (fresh) | 0.0 | — | — | 4.00 | 131 |
| | 12.5 | 23.5 | 223 | 0.01 | 804 |
| | 13.2 | 23.6 | 217 | 0.04 | 729 |
| | 15.0 | 23.4 | 212 | 0.02 | 1052 |
| Amberlyst ®-35 (fresh) | 0.0 | — | — | 3.99 | — |
| | 18.5 | 22.8 | 321 | 0.11 | 713 |
| | 20.8 | 23.1 | 326 | 0.10 | 732 |
| | 22.5 | 23.1 | 326 | 0.10 | 99 |

Table 1 demonstrates that fresh ion exchange are effective at removing DEHA from butadiene streams.

EXAMPLE 2

A butadiene feed containing DEHA was charged to a feed tank containing pure crystalline TBC, and the tank was well agitated. The feed was then run through a 50 mL stainless steel up-flow reactor. The reactor was operated at 85 psig and at ambient temperature. For each run, 50 mL of resin were charged to the reactor. Periodically, a sample of the reactor effluent was collected and analyzed. Table 2 details the results.

TABLE 2

| Resin | Time (hr) | Temp. (° C.) | Feed Rate (g/hr) | DEHA in effluent (ppm) | TBC in effluent (ppm) | Water in effluent (ppm) |
|---|---|---|---|---|---|---|
| Amberlyst ® 35 (fresh) | 0.0 | — | — | 3.66 | 21.0 | 700 |
| | 24.7 | 21.8 | 318 | 0.05 | 19.0 | 366 |
| | 26.7 | 22.2 | 313 | 0.00 | 14.0 | 719 |
| | 28.5 | 22.7 | 316 | 0.11 | 16.0 | 725 |
| Amberlyst ® 35 (fresh) | 0.0 | — | — | 6.70 | 9.0 | 995 |
| | 31.2 | 23.6 | 317 | 0.15 | 14.7 | 674 |
| | 35.0 | 23.4 | 324 | 0.32 | 9.0 | 995 |
| | 37.1 | 23.2 | 306 | 1.00 | 9.0 | 673 |
| Amberlyst ® 35 (spent)[1] | 0.0 | — | — | 11.16 | 9.0 | 334 |
| | 1.8 | 23.2 | 342 | 2.30 | 6.0 | 528 |
| | 3.7 | 23.3 | 336 | 0.35 | 11.0 | 758 |
| | 6.0 | 23.5 | 328 | 0.25 | 8.0 | 524 |
| Amberlyst ® 15 (spent)[2] | 0.0 | — | — | 11.3 | 14.0 | 354 |
| | 1.6 | 23.1 | 304 | 0.09 | 11.0 | 1154 |
| | 3.6 | 23.3 | 303 | 0.21 | 5.0 | 561 |
| | 6.0 | 23.5 | 303 | 0.51 | 11.0 | 624 |

[1]Spent by use in the preparation of methyl-tert-butyl ether (MTBE).
[2]Spent by use in the preparation of methyl-tert-butyl ether (MTBE).

Table 2 shows that both fresh and spent ion exchange resins are effective at removing DEHA from the butadiene streams. In addition, Table 2 also shows that while the ion exchange resins remove DEHA from the butadiene streams, the resins remove only a minimal amount of TBC from the butadiene streams.

EXAMPLE 3

For comparison, various resins were tested to determine whether they were also capable of removing DEHA from another hydrocarbon, such as cyclohexane. For this example, DEHA was dissolved in cyclohexane, and then mixed with 20 grams of each of the resins listed below. The resins were then filtered, and each solution was then analyzed for nitrogen. Table 3 details the results.

TABLE 3

| Resin | Nitrogen (ppm) |
|---|---|
| no resin | 47.3 |
| Amberlyst ®-15 | <1 |
| Amberlyst ®-35 | <1 |
| Amberlyst ®-36 | <1 |
| Amberlyst ®-XN-1010 | <1 |
| Dowex ®-50WX2 | 2.3 |

Table 3 shows that the ion exchange resins are capable of removing DEHA from other hydrocarbon sources, such as cyclohexane.

Although illustrative embodiments have been shown and described, a wide range of modification, changes, and substitution is contemplated in the foregoing disclosure. In some instances, some features of the disclosed embodiments may be employed without a corresponding use of the other features. Accordingly, it is appropriate that the appended claims be construed broadly and in a manner consistent with the scope of the invention.

What is claimed is:

1. A method of removing diethylhydroxylamine from butadiene streams comprising:

a. providing a stream comprising primarily butadiene and a minor amount of diethylhydroxylamine;

b. contacting the stream with an ion exchange resin to effectuate removal of the diethylhydroxylamine from the stream; and c. adding a sufficient amount of tert-butylcatechol to the stream to prevent polymerization of the butadiene.

2. The method of claim 1, wherein the stream is contacted with the ion exchange resin at a temperature from about 0° C. to about 110° C.

3. The method of claim 1, wherein the stream is contacted with the ion exchange resin at a temperature from about 15° C. to about 50° C.

4. The method of claim 1, wherein the stream is contacted with the ion exchange resin at a pressure from about atmospheric pressure to about 2000 psig.

5. The method of claim 1, wherein the stream is contacted with the ion exchange resin at a pressure from about 50 psig to about 150 psig.

6. The method of claim 1, wherein the ion exchange resin is selected from the group consisting of Amberlyst®-15, Amberlyst®-35, Amberlyst®-36, Amberlyst® XN-1010, and Dowex®-50WX2.

7. The method of claim 1, wherein the ion exchange resin is a fresh resin.

8. The method of claim 1, wherein the ion exchange resin is a spent resin.

9. The method of claim 1, wherein the stream comprises at least about 5 ppm of tert-butylcatechol.

10. A method of removing diethylhydroxylamine from butadiene streams comprising:

a. providing a stream comprising primarily butadiene and a minor amount of diethylhydroxylamine;

b. mixing the stream with a sufficient amount of tert-butylcatechol to prevent polymerization of the butadiene; and c. contacting the stream with an ion exchange resin to effectuate removal of the diethylhydroxylamine from the stream.

11. The method of claim 10, wherein the stream is contacted with the ion exchange resin at a temperature from about 0° C. to about 1100° C.

12. The method of claim 10, wherein the stream is contacted with the ion exchange resin at a temperature from about 15° C. to about 500° C.

13. The method of claim 10, wherein the stream is contacted with the ion exchange resin at a pressure from about atmospheric pressure to about 2000 psig.

14. The method of claim 10, wherein the stream is contacted with the ion exchange resin at a pressure from about 50 psig to about 150 psig.

15. The method of claim 10, wherein the ion exchange resin is selected from the group consisting of Amberlyst®-15, Amberlyst®-35, Amberlyst®-36, Amberlyst® XN-1010, and Dowex®-50WX2.

16. The method of claim 10, wherein the ion exchange resin is a fresh resin.

17. The method of claim 10, wherein the ion exchange resin is a spent resin.

18. The method of claim 10, wherein prior to diethylhydroxylamine removal, the stream comprises at least about 5 ppm of tert-butylcatechol.

19. A method of removing diethylhydroxylamine from hydrocarbon streams comprising:

a. providing a stream comprising a hydrocarbon, or mixtures thereof, and a minor amount of diethylhydroxylamine, relative to the amount of the hydrocarbon in the stream; and b. contacting the stream with an ion exchange resin to effectuate removal of the diethylhydroxylamine from the stream.

20. The method of claim 19, wherein the hydrocarbon comprises an unsaturated hydrocarbon.

21. The method of claim 19, wherein the hydrocarbon comprises butadiene.

22. The method of claim 21, further comprising the step of mixing the stream with a sufficient amount of tert-butylcatechol to prevent polymerization of the butadiene.

23. The method of claim 22, wherein the stream is contacted with the ion exchange resin at a temperature from about 0° C. to about 110° C.

24. The method of claim 22, wherein the stream is contacted with the ion exchange resin at a temperature from about 15° C. to about 50° C.

25. The method of claim 22, wherein the stream is contacted with the ion exchange resin at a pressure from about atmospheric pressure to about 2000 psig.

26. The method of claim 22, wherein the stream is contacted with the ion exchange resin at a pressure from about 50 psig to about 150 psig.

27. The method of claim 19, wherein the ion exchange resin is selected from the group consisting of Amberlyst®-15, Amberlyst®-35, Amberlyst®-36, Amberlyst® XN-1010, and Dowex®-50WX2.

28. The method of claim 19, wherein the ion exchange resin is a fresh resin.

29. The method of claim 19, wherein the ion exchange resin is a spent resin.

30. The method of claim 22, wherein the stream comprises at least about 5 ppm of tert-butylcatechol.

\* \* \* \* \*